US00PP31333P3

(12) United States Plant Patent
Hoogkamp

(10) Patent No.: US PP31,333 P3
(45) Date of Patent: Jan. 7, 2020

(54) ***SPATHIPHYLLUM* PLANT NAMED 'SPAMOZO'**

(50) Latin Name: ***Spathiphyllum* Schott.**
Varietal Denomination: Spamozo

(71) Applicant: Timothy Johan Herman Hoogkamp, Doetinchem (NL)

(72) Inventor: Timothy Johan Herman Hoogkamp, Doetinchem (NL)

(73) Assignee: Nubilus B.V., Naaldwijk (NL)

( * ) Notice: Subject to any disclaimer, the term of this patent is extended or adjusted under 35 U.S.C. 154(b) by 0 days.

(21) Appl. No.: 16/350,172

(22) Filed: Oct. 10, 2018

(65) Prior Publication Data

US 2019/0116707 P1 Apr. 18, 2019

Related U.S. Application Data

(60) Provisional application No. 62/707,025, filed on Oct. 17, 2017.

(51) Int. Cl.
*A01H 5/02* (2018.01)
*A01H 6/00* (2018.01)

(52) U.S. Cl.
USPC ..... Plt./364
CPC ..... *A01H 6/00* (2018.05); *A01H 5/02* (2013.01)

(58) Field of Classification Search
USPC ..... Plt./364
CPC ..... A01H 6/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Spathiphyllum* plant named 'Spamozo', characterized by its upright, outwardly arching and uniform plant habit; freely clumping growth habit; bushy and dense plants; glossy dark green-colored leaves; large white-colored spathes that are positioned just above the foliar plane on strong and erect scapes; and good inflorescence longevity.

2 Drawing Sheets

Botanical designation: *Spathiphyllum* Schott.
Cultivar denomination: 'SPAMOZO'.

BACKGROUND OF THE INVENTION

The present invention relates to a new and distinct cultivar of *Spathiphyllum* plant, botanically known as *Spathiphyllum* Schott. and hereinafter referred to by the cultivar name 'Spamozo'.

The new *Spathiphyllum* plant is a product of a controlled breeding program conducted by the Inventor in Naaldwijk, The Netherlands. The objective of the breeding program is to create new year-round flowering *Spathiphyllum* plants that have glossy dark green-colored leaves, large white-colored spathes and good postproduction longevity.

The new *Spathiphyllum* plant originated from a cross-pollination made by the Inventor in September, 2010 of a proprietary selection of *Spathiphyllum* Schott. identified as code number 20071360-36, not patented, as the female, or seed, parent with a proprietary selection of *Spathiphyllum* Schott. identified as code number 20071584-28, not patented, as the male, or pollen, parent. The new *Spathiphyllum* plant was discovered and selected by the Inventor as a single plant within the progeny of the stated cross-pollination in a controlled greenhouse environment in Naaldwijk, The Netherlands in May, 2011.

Asexual reproduction of the new *Spathiphyllum* plant by in vitro meristem culture in a controlled environment in Naaldwijk, The Netherlands since May, 2011 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spamozo'. These characteristics in combination distinguish 'Spamozo' as a new and distinct *Spathiphyllum* plant:

1. Upright, outwardly arching and uniform plant habit.
2. Freely clumping growth habit; bushy and dense plants.
3. Glossy dark green-colored leaves.
4. Large white-colored spathes that are positioned just above the foliar plane on strong and erect scapes.
5. Good inflorescence longevity.

Plants of the new *Spathiphyllum* differ from plants of the female parent selection in the following characteristics:

1. Plants of the new *Spathiphyllum* are more compact than plants of the female parent selection.
2. Leaves of plants of the new *Spathiphyllum* are more durable than leaves of plants of the female parent selection.

Plants of the new *Spathiphyllum* differ from plants of the male parent selection in the following characteristics:

1. Plants of the new *Spathiphyllum* are more compact than plants of the male parent selection.
2. Leaves of plants of the new *Spathiphyllum* are more durable than leaves of plants of the male parent selection.

Plants of the new *Spathiphyllum* can also be compared to plants of *Spathiphyllum* Schott. 'Sparanke', disclosed in U.S. Plant Pat. No. 21,294. In side-by-side comparisons, plants of the new *Spathiphyllum* differ from plants of 'Sparanke' in the following characteristics:

1. Plants of the new *Spathiphyllum* are more compact than plants of 'Sparanke'.
2. Leaves of plants of the new *Spathiphyllum* are smoother than and not as rough as leaves of plants of 'Sparanke'.
3. Plants of the new *Spathiphyllum* have larger inflorescences than plants of 'Sparanke'.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet is a side perspective view of a typical plant of 'Spamozo' grown in a container.

The photograph on the second sheet is a close-up view of a typical inflorescence of 'Spamozo'.

DETAILED BOTANICAL DESCRIPTION

The aforementioned photographs and following observations and measurements describe plants grown during the late spring in 14-cm containers in a glass-covered greenhouse in Naaldwijk, The Netherlands and under cultural practices typical of commercial *Spathiphyllum* production. During the production of the plants, day temperatures ranged from 22° C. to 28° C., night temperatures ranged from 20° C. to 22° C. and light levels averaged 5 klux. Plants were six months old when the photographs and the detailed description were taken. In the following description, color references are made to The Royal Horticultural Society Colour Chart, 2015 Edition, except where general terms of ordinary dictionary significance are used.

Botanical classification: *Spathiphyllum* Schott. 'Spamozo'.

Parentage:

*Female, or seed, parent.*—Proprietary selection of *Spathiphyllum* Schott. identified as code number 20071360-36, not patented.

*Male, or pollen, parent.*—Proprietary selection of *Spathiphyllum* Schott. identified as code number 20071584-28, not patented.

Propagation:

*Type.*—By in vitro meristem culture.

*Time to initiate roots, summer.*—About twelve days at temperatures about 23° C.

*Time to initiate roots, winter.*—About 13 days at temperatures about 23° C.

*Time to produce a rooted young plant, summer.*—About 215 days at temperatures about 21° C.

*Time to produce a rooted young plant, winter.*—About 240 days at temperatures about 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately branching, medium density.

Plant description:

*Plant and growth habit.*—Upright and outwardly arching plant habit; overall plant shape, broadly inverted triangle; moderately vigorous growth habit; moderate growth rate.

*Clumping habit.*—Freely clumping habit, bushy and dense growth habit; about 14 clumps develop per plant.

*Plant height, from soil level to top of leaf plane.*—About 41.9 cm.

*Plant height, from soil level to top of inflorescences.*—About 48.1 cm.

*Plant diameter or spread.*—About 64.5 cm.

*Leaf description.*—Arrangement: Alternate; simple. Length: About 26.4 cm. Width: About 13.1 cm. Shape: Ovate. Apex: Apiculate. Base: Short attenuate. Margin: Entire; moderately undulate. Texture and luster, upper surface: Smooth, glabrous; glossy. Texture and luster, lower surface: Smooth, glabrous; moderately glossy. Venation pattern: Pinnate. Color: Developing leaves, upper surface: More intense than close to between 143A and 144A. Developing leaves, lower surface: Close to between 139C and 143C. Fully expanded leaves, upper surface: Close to between NN137A and 147A; venation, close to 143A. Fully expanded leaves, lower surface: Close to NN137D; venation, close to 144B. Petioles: Length (excluding geniculum): About 11.7 cm. Diameter, just below geniculum: About 5.5 mm. Diameter, at plant base: About 7 mm. Strength: Strong. Texture and luster, upper and lower surfaces: Smooth, glabrous; matte. Color, upper surface: Close to 149D. Color, lower surface: Close to 137B. Geniculum length: About 3 cm. Geniculum diameter: About 6 mm. Geniculum texture and luster, upper and lower surfaces: Smooth, glabrous; matte. Geniculum color, upper and lower surfaces: Close to 138A. Wing length: About 11.5 cm. Wing diameter: About 1 cm. Wing color: Close to 138A; towards the margins, close to 143C.

Inflorescence description:

*Inflorescence arrangement and flowering habit.*—Moderately to strongly cupped erect spathes with columnar spadices held above the foliar plane on strong and erect scapes; flowering structures arise from leaf axils; plants begin flowering about 26 weeks after planting; freely and continuous flowering year-round under greenhouse conditions in The Netherlands; about three inflorescences develop per plant.

*Fragrance.*—Moderately fragrant; fragrance, sweet and pleasant.

*Inflorescence longevity.*—Inflorescences last more than three weeks on the plant; inflorescences persistent.

*Spathe.*—Length: About 19.5 cm. Width: About 10 cm. Depth: About 6.1 cm. Shape: Ovate to elliptic. Apex: Apiculate; twisting and curled. Base: Attenuate. Margin: Entire; not undulate. Texture and luster, front surface: Smooth, glabrous; slightly leathery; slightly glossy. Texture and luster, rear surface: Smooth, glabrous; slightly leathery; moderately glossy. Color: When developing, front surface: Close to NN155A; apex, close to 144C. When developing, rear surface: Close to NN155A; towards the apex and main vein, close to 144A to 144B. Fully developed, front surface: Close to NN155C; towards the apex, close to 144B; color does not change with development. Fully developed, rear surface: Close to NN155D; towards the apex and main vein, close to 144A to 144B; color does not change with development.

*Spadix.*—Length: About 8.5 cm. Diameter: About 1.6 cm. Shape: Columnar, tapering towards the apex; apex, obtuse; base, obtuse; cross-section, rounded. Aspect: Close to erect, about 5° from scape axis. Color, immature: Close to 150D. Color, mature: Close to between 158C and 158D. Flowers: Quantity per spadix: Numerous, about 250. Shape: Rounded. Height: About 3 mm. Diameter: About 4 mm. Anther color: Close to NN155B to NN155C. Pollen amount: Moderate. Pollen color: Close to 155B. Stigma color: Close to 158D. Ovary color: Close to 158C.

*Scapes.*—Length: About 42.8 cm. Diameter: About 7 mm. Strength: Strong. Aspect: Erect. Texture and luster: Smooth, glabrous; matte to slightly glossy. Color: Close to 143C.

*Seeds and fruits.*—To date, seed and fruit development have not been observed on plants of the new *Spathiphyllum.*

Disease & pest resistance: To date, plants of the new *Spathiphyllum* have not been observed to be resistant to pathogens or pests common to *Spathiphyllum* plants.

Temperature tolerance: Plants of the new *Spathiphyllum* have been observed to be tolerant to temperatures ranging from about 5° C. to about 40° C. and to be suitable for USDA Hardiness Zones 10 to 13.

It is claimed:

1. A new and distinct *Spathiphyllum* plant named 'Spamozo' as illustrated and described.

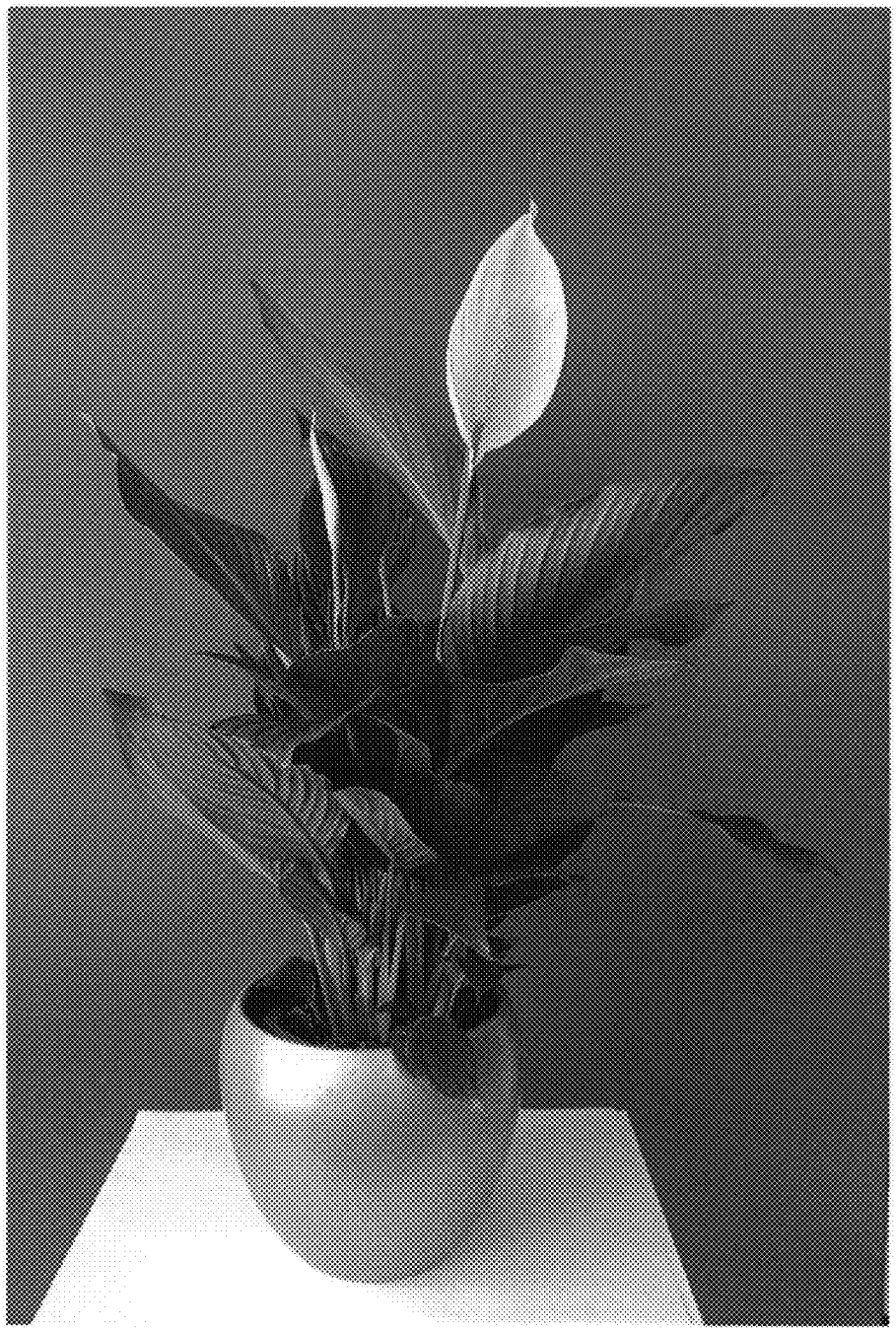

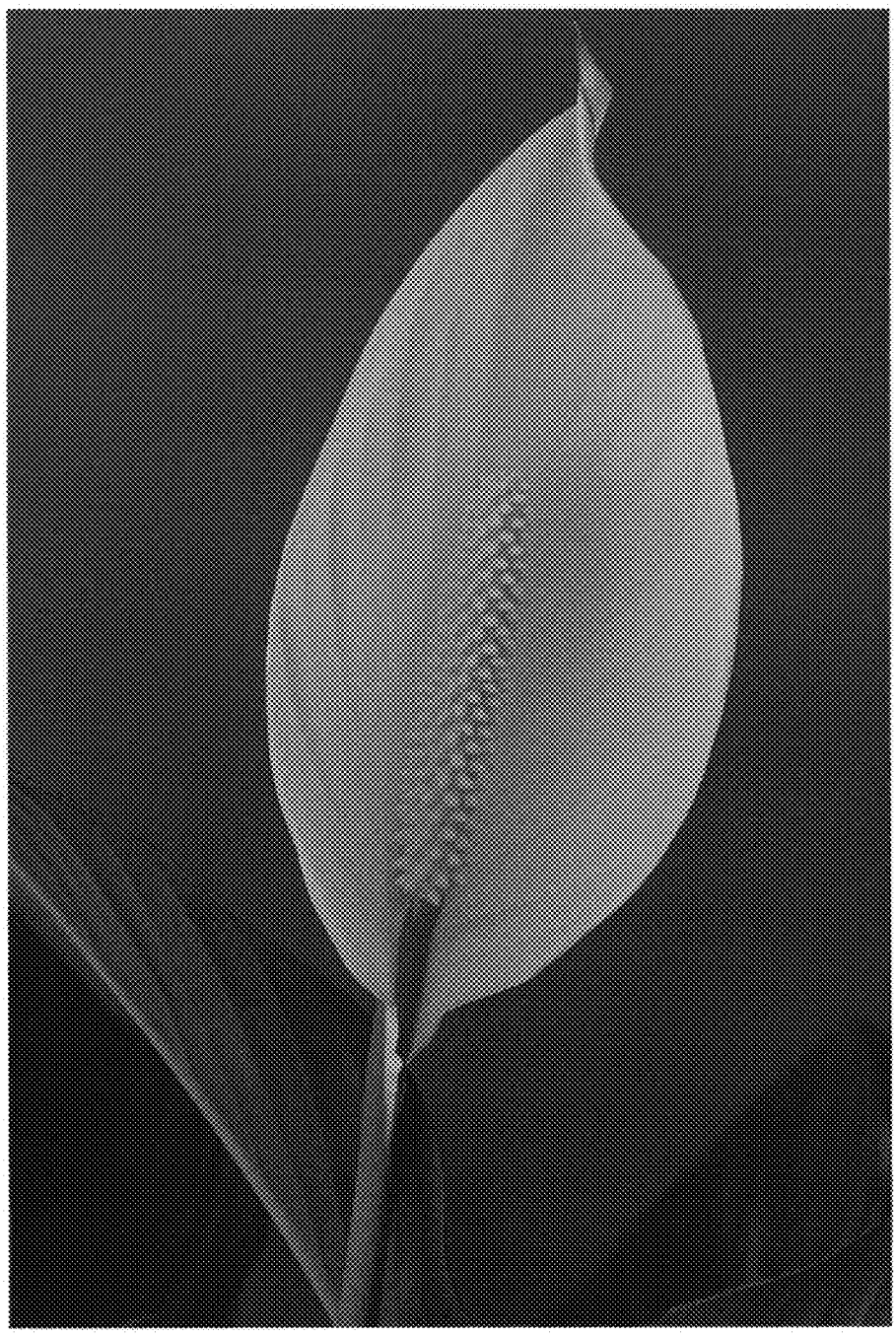

* * * * *